United States Patent [19]
Hogg

[11] Patent Number: 5,312,216
[45] Date of Patent: May 17, 1994

[54] ARITFICIAL JOINT PROSTHESIS

[76] Inventor: John M. Hogg, 122 King William, San Antonio, Tex. 78204

[21] Appl. No.: 858,225

[22] Filed: Mar. 26, 1992

Related U.S. Application Data

[63] Continuation-in-part of Ser. No. 723,426, Jun. 28, 1991, abandoned.

[51] Int. Cl.$^5$ ................................................ A61F 2/32
[52] U.S. Cl. .................................................... 623/22
[58] Field of Search ...................... 623/16, 18, 19, 20, 623/22, 23

[56] References Cited

U.S. PATENT DOCUMENTS

| | | | |
|---|---|---|---|
| 3,140,712 | 7/1964 | Hunter | 623/18 |
| 3,916,451 | 11/1975 | Buechel et al. | 623/22 |
| 3,982,281 | 9/1976 | Giliberty | 623/23 |
| 4,135,517 | 1/1979 | Reale | 606/89 |
| 4,172,296 | 10/1979 | D'Errico | 623/22 |
| 4,180,873 | 1/1980 | Fixel | 623/22 |
| 4,214,322 | 7/1980 | Kraus | 623/18 |
| 4,408,360 | 10/1983 | Keller | 623/23 |
| 4,502,160 | 3/1985 | Moare et al. | 623/18 |
| 4,538,306 | 9/1985 | Dorre et al. | 623/18 |
| 4,553,273 | 11/1985 | Wu | 623/18 |
| 4,678,472 | 7/1987 | Noiles | 623/22 |
| 4,686,971 | 8/1987 | Harris et al. | 606/99 |
| 4,892,546 | 1/1990 | Kotz et al. | 623/18 |
| 5,026,399 | 6/1991 | Engelbrecht et al. | 623/18 |
| 5,032,130 | 7/1991 | Schelhas et al. | 623/23 |

FOREIGN PATENT DOCUMENTS

| | | | |
|---|---|---|---|
| 2501080 | 7/1976 | Fed. Rep. of Germany | 623/18 |
| 3605630 | 9/1987 | Fed. Rep. of Germany | 623/16 |

Primary Examiner—David Isabella

[57] ABSTRACT

The currently used method for the replacement of joints greatly limits how the joint can be used. This invention overcomes these limitations returning the joint to full normal use. This is accomplished by my development of a system of joints that stay intact up to just short of bone breaking. At this point it will pop out. It can then be reset simularly to resetting a normal joint. This invention also includes a system for total limb replacement including limited action joints. Also included are various clamps to assist the surgeon.

2 Claims, 4 Drawing Sheets

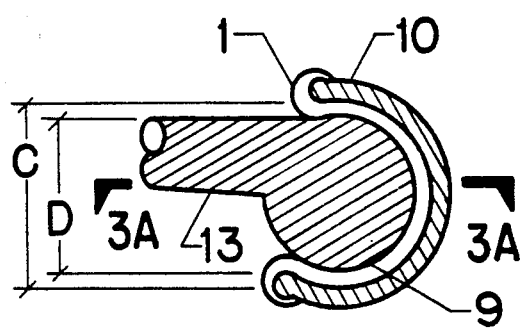
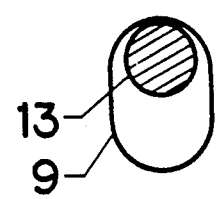
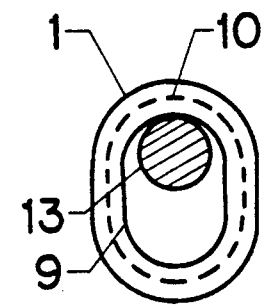
FIG. 3  FIG. 4  FIG. 5
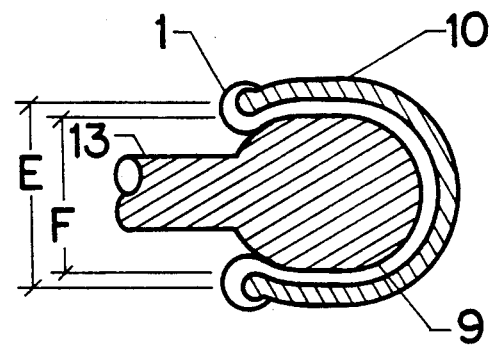
FIG. 3A

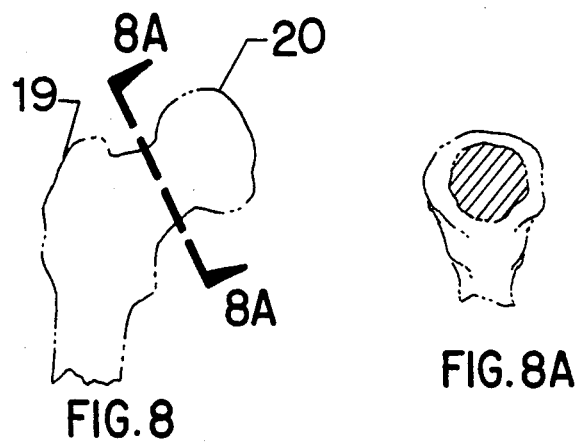
FIG. 8
FIG. 8A
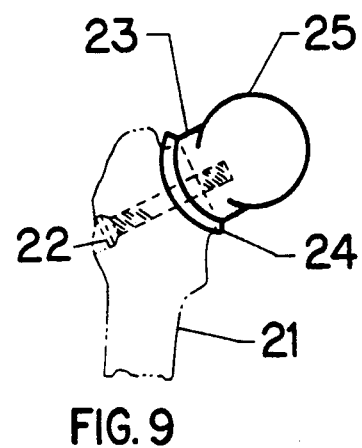
FIG. 9
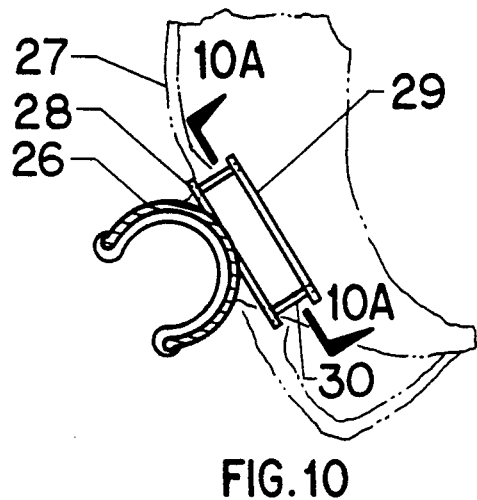
FIG. 10
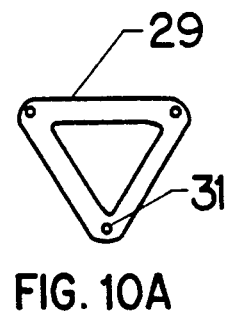
FIG. 10A
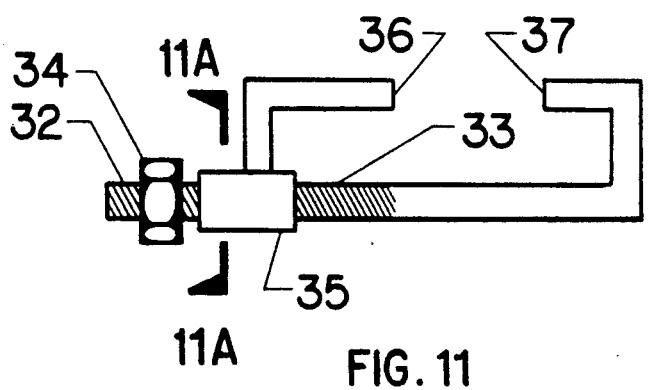
FIG. 11
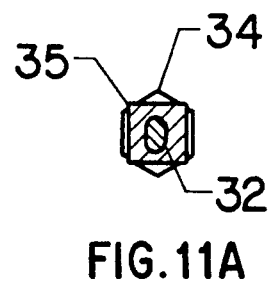
FIG. 11A

ARTIFICIAL JOINT PROSTHESIS

This application is a continuation-in-part of Ser. No. 07/723,426 filed on Jun. 28, 1991, now abandoned.

BRIEF SUMMARY

The prosthesis and limited rotational prosthesis joints combine four major disciplines: Medical, Electrical, Mechanical and Electronic Engineering. This invention, or device, will insure that the joint when locked in place cannot dislocate itself until excessive force is reached, the same force necessary to dislocate a normal joint.

BRIEF DESCRIPTION OF THE DRAWINGS

In the accompanying diagrammatic drawings which illustrate the invention:

FIG. 3 is a cross section of a limited rotational joint prosthesis;

FIG. 3A is a section that is shown as Section 3A—3A in FIG. 3;

FIG. 4 is an end view of the ball and shaft in FIG. 3;

FIG. 5 is an end view of the complete joint in FIG. 3;

FIG. 8 is a perspective view of the depicting a resection line for the femoral joint;

FIG. 8A is a sectional drawing of Section 3A—3A of FIG. 3;

FIG. 9 is a perspective view of an alternative embodiment of a femoral joint;

FIG. 10 is a perspective view of a metal socket attached to the pelvic bone;

FIG. 10A is a end view of the plate in FIG. 10;

FIG. 11 is an alternative embodiment for a installation clamp

FIG. 11A is a cross section of the installation clamp in FIG. 11.

DESCRIPTION OF PREFERRED EMBODIMENTS

With this invention, or device, the ball will only pop out when the disengagement force approaches a critical amount that is just short of breaking the bone. Since the metal socket does not allow x-rays to see the condition of the artificial cartilage, electronic chips can be installed in the outer surface of the artificial cartilage next to the outer shell. When the artificial cartilage wears thin enough for the metal ball to contact or press on a chip a signal, either sound or electronic, would be emitted alerting the doctor that replacement may soon be required. The chip would have its built-in source of electricity such as two dissimilar metals that produce electricity when brought in electrical contact with each other. (An example is an ionized zinc plate with a negative potential of 0.758 volts and an ionized copper plate with a positive potential of 0.344 volts having a differential of 1.1 volts between the plates.) The ball would either complete the circuit by shorting across two contact points or pressing on a built-in pressure switch mounted on the chip. The chip would be a radio frequency oscillator. A sensitive receiver of the same frequency would be used to detect the signal. A standard oscillator chip of suitable size, now available from such companies as Texas Instruments, would have the necessary contact points or pressure switch and voltage source added. Such oscillator chip should be of as low drain as possible.

Figure 1:
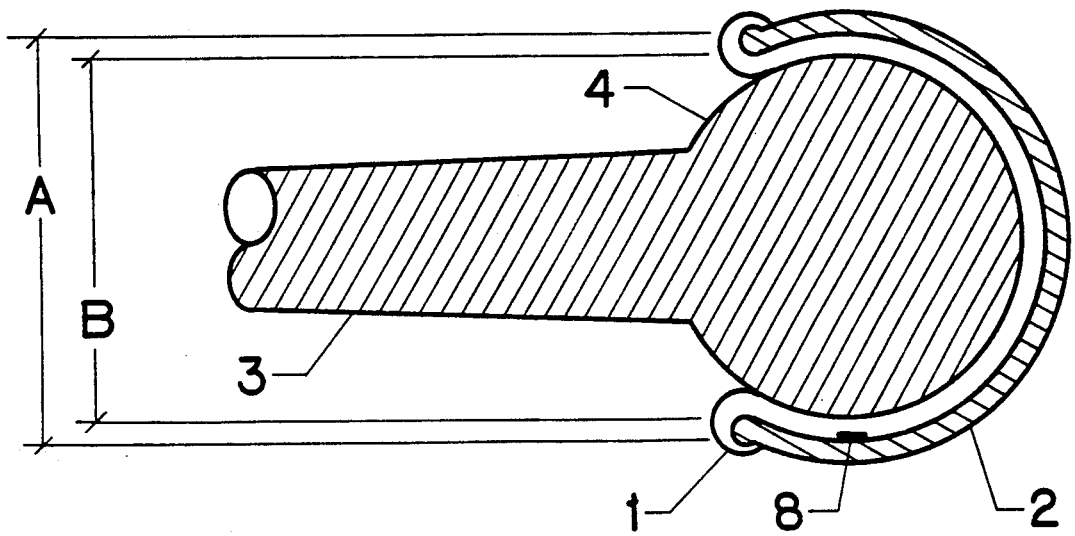
FIG. 1 is a cross section of the joint.
Figure 2:
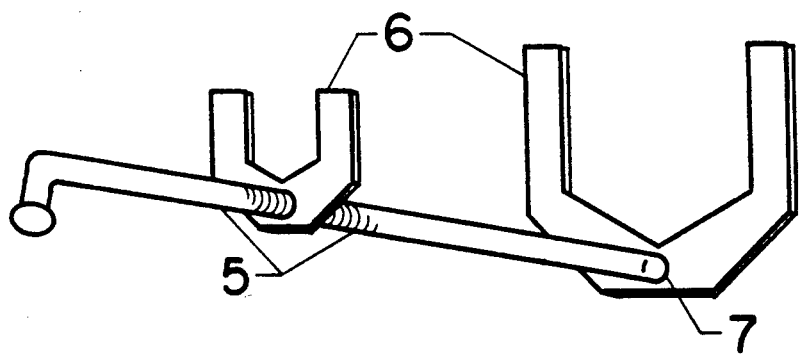
FIG. 2 is a general illustration of the installation screw clamp for pressing the ball into the socket.

FIG. 1 is a cross section of the joint where 3 is the shaft, 4 is the ball, 1 is the artificial cartilage, and 2 is the outer shell. Dimension A is the diameter of the opening of the outer shell. Dimension B is the diameter of the ball. The relation of these two and the material and thickness of the artificial cartilage determines the forces necessary to cause the ball to pop out. Several electronic chips can be located around the outer surface of the artificial cartilage. 8 shows one such electronic chip. FIG. 2 is a general drawing of an installation screw clamp to help press the ball into the socket. 6 shows the general configuration of the two braces for the clamp. 5 is a threaded rod screwing through the smaller brace 6 and passing through the larger brace at 7 with an enlarged head to the rear of the larger brace. Hip and shoulder joints require a shaft that curves to almost a right angle in order that it may be inserted into, clamped onto, or attached to the bone or other device. Other types of circular motion joints have a shaft that comes straight out from the ball for use to replace such joints as the ankle. It would be attached similarly to the preceding joint.

FIG. 3 is a limited rotational prosthesis joint differing from the joint in FIG. 1 in that the shaft has one edge tangent to the circumference of the ball which limits how far it will rotate in the socket. FIG. 3 is a cross section of the limited prosthesis joint. Dimension C is the diameter of the opening of the outer socket. Dimension D is the diameter of the ball. The relation of these two and the material and thickness of the artificial cartilage determines the force necessary to cause the ball to pop out. 1 is the artificial cartilage. 10 is the metal outer shell. 13 is the metal shaft. 9 is the metal ball. FIG. 3-A is a cross section that is shown as section 3A—3A in FIG. 3. FIG. 4 is an end on view of the ball and shaft in FIG. 3 above; 9 is the metal ball and 13 is in the shaft. FIG. 5 is an end on view of the complete joint shown in FIG. 3 above; 9 is the metal ball, 13 is the shaft, 10 is the outer shell and 1 is the lip of the cartilage. The elongated sides shown in all views limit rotation in various directions. Diameter E is the diameter of the opening of the outer shell. Diameter F is the diameter of the ball. The relation of these two and the material and thickness in the artificial cartilage determines the force necessary to cause the ball to pop out. 1 is the artificial cartilage. 10 is the metal outer shell. 13 is the metal shaft. 9 is the metal ball.

For Knee and Elbow Joints

The limited rotational prosthesis joint can be mounted facing either the thigh bone or the bones of the lower leg. Elbow replacement would follow a similar pattern. It can be clamped on, spiked into the bones in both directions, or screwed on according to the surgeon's determination.

Other examples of usage in limited rotational prosthesis joints would be fingers, toes, and other small bones in the extremities.

Total Limb Replacement

Hip to Knee or Shoulder to Elbow

Figure 6:
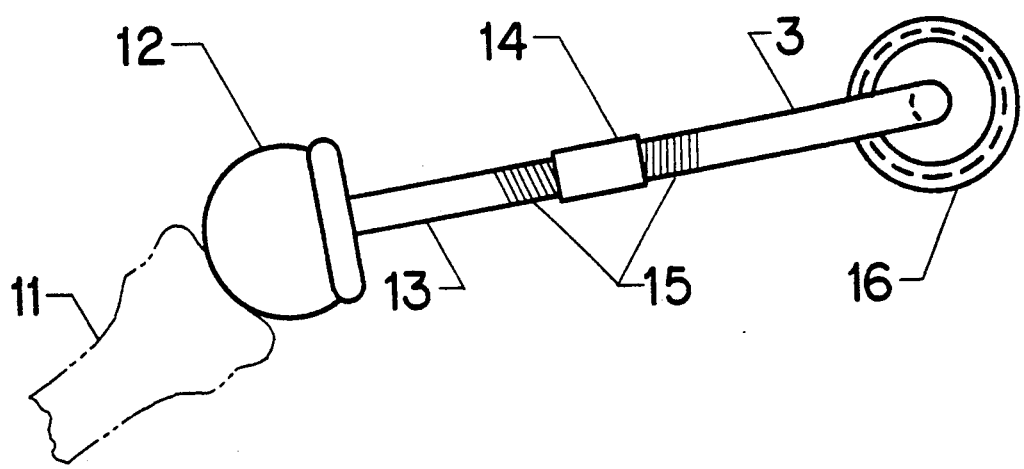
FIG. 6 is a perspective view of a total joint replacement for the upper leg or upper arm.
Figure 7:
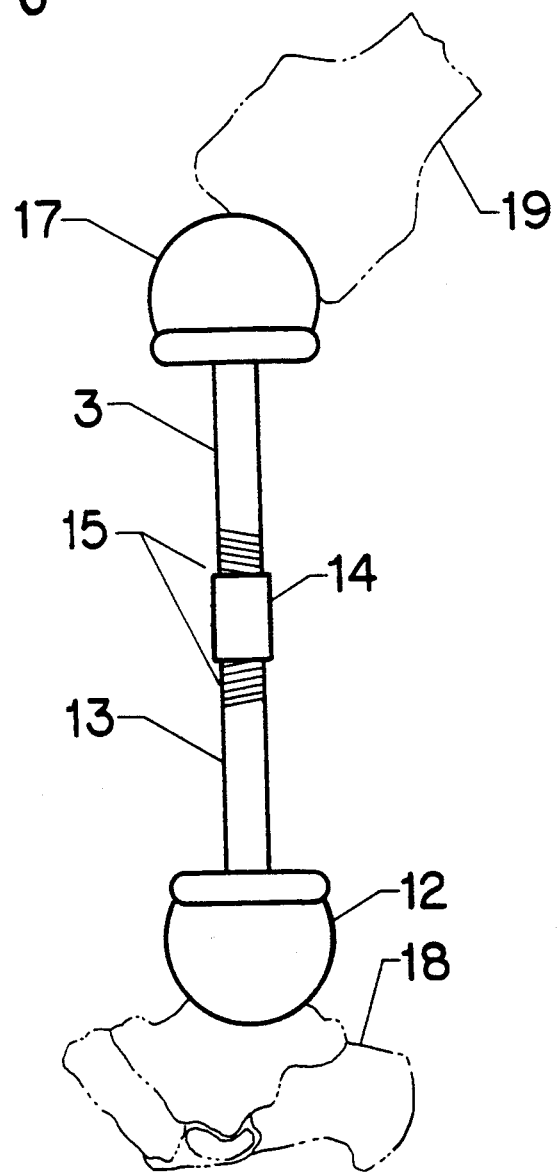
FIG. 7 is a perspective view of a total joint replacement for the lower leg.

FIG. 6 is an assembly view of the hip to knee or shoulder to elbow replacement. 16 is a standard prosthesis joint, 12 is a limited rotational prosthesis joint. 3 is the upper shaft and 13 is the lower shaft which are treated in order for the flesh to attach to them. Ends 15 are very fine threaded to screw into the turnbuckle 14 (these ends are threaded counter clockwise to each other). These threads and the turnbuckle are not treated.

The limited rotational prosthesis joint 12 is attached to the lower leg bone so that it stops the leg going past straight. This is the same type of joint as shown in FIG. 3. It has a straight shaft 13 to be coupled to shaft 3. For a person whose growth is not complete the length can be adjusted from time to time. Turnbuckles would use locking nuts on each end to avoid accidental turning. A small incision would be required to adjusted from time to time. Turnbuckles would use locking nuts on each end to avoid accidental turning. A small incision would be required to make an adjustment. 11 indicates the tibia or ulna.

Knee to Ankle (Elbow and wrist may be substituted for knee and ankle respectively).

In FIG. 7 13, 14, 15, and 3 are the same as in FIG. 6 above except that shaft 3 comes straight out of ball joint 12 which is attached to the ankle 18. Ball joint 17 which is a limited rotational prosthesis joint as shown in FIG. 3, and attached to the thigh bone 19 and pointed down with its shaft 3 connected to shaft 13. For complete bone replacement of the leg, the knee limited rational prosthesis have shafts so that it can be connected to the hip and ankle prosthesis. There are many variations and possibilities for other uses of clamps depending on what bone structure is left. FIG. 8 shows the femur 19 with 20 the head of the bone. 8A—8A is a possible cut off line. FIG. 9 shows the modified femur 21 with a bolt 22 holding the metal shaft 23 with its flared base 24, these two are held or temporarily clamped in place and serve as a guide for drilling the hole for bolt 22 through the bone 21. The metal shaft 23 with its flared base 24 is then clamped in place when bolt 22 is inserted through it and screwed into ball 25. FIG. 10 shows a method of clamping the metal socket 26 of the artificial joint to the pelvic bone 27. 28 is a plate with three lugs attached to the outside of the metal socket 26. This avoids having bolts through the socket 26 and would allow the joint to be preassembled if desired. Triangular plate 29, FIG. 10-A, shows the detail of the plate of section 10A—10A in FIG. 10, it is placed on the other side of the pelvic bone 27 opposite the three lugs of 28, and attached by bolts 30 which pass through the pelvic bone 27 screwing into holes 31 of plate 29 of FIG. 10-A. FIG. 11 shows a clamp that may be used to assist the surgeon in installing or resetting the ball in the socket of a prosthesis joint. 32 is the shaft and 33 shows the section that is threaded. 34 is a nut used to apply the required pressure to the slide 35 to press points 36 and 37 together thus pushing the ball back into the socket. FIG. 11-A is the section 11A—11A shown in FIG. 11 and shows how the shaft 32 has flattened sides so the slide 35 will keep the points 36 and 37 lined up. When resetting, small incisions may be required in the front and rear of the hip to allow points 36 and 37 to press on the ball and socket when resetting a prosthesis joint.

I claim:

1. Artificial joints comprising an implantable ball and socket prosthesis consisting of an outer cup shaped metal shell having an outer surface configured to engage a natural cotyloid cavity and a cup shaped inner surface for receipt of a complimentary shaped bearing element; an artificial cartilage to be affixed to the inner surface serving as the bearing element, the force required for popout separation is to be predetermined by the experts: a sensor means disposed in the bearing element, said sensor means including an activating means which activates when the bearing element wears to a point that the force of the joint ball head makes contact with the sensor means to activate the activating means whereby once the activating means is activated said sensor means emits and electronic signal which may be picked up by a receiver.

2. These artificial joints as recited in claim 1, where said prosthesis further comprising fastening means for attachment to the bone.

* * * * *

UNITED STATES PATENT AND TRADEMARK OFFICE
CERTIFICATE OF CORRECTION

PATENT NO. : 5,312,216
DATED : May 17, 1994
INVENTOR(S) : John M. Hogg

It is certified that error appears in the above-identified patent and that said Letters Patent is hereby corrected as shown below:

Column 1, line 64, change ".)" to --).--

Signed and Sealed this

Seventeenth Day of September, 1996

Attest:

BRUCE LEHMAN

Attesting Officer        Commissioner of Patents and Trademarks